(12) United States Patent
Nagai

(10) Patent No.: US 6,365,106 B1
(45) Date of Patent: Apr. 2, 2002

(54) SHEATH FLOW CELL AND BLOOD ANALYZER USING THE SAME

(75) Inventor: Takaaki Nagai, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/488,552

(22) Filed: Jan. 21, 2000

(30) Foreign Application Priority Data

Jan. 21, 1999 (JP) .......................................... 11-013293

(51) Int. Cl.⁷ .............................................. G01N 33/00
(52) U.S. Cl. ........................... 422/73; 422/102; 436/63; 436/165; 356/246
(58) Field of Search .............................. 422/73, 82.05, 422/82.09, 102; 436/63, 164, 165; 356/39, 73, 246, 243.1, 243.2

(56) References Cited

U.S. PATENT DOCUMENTS

| | | | | |
|---|---|---|---|---|
| 3,649,829 A | * | 3/1972 | Randolph | |
| 5,079,959 A | * | 1/1992 | Miyake et al. | 73/864.85 |
| 5,159,403 A | * | 10/1992 | Kosaka | 356/246 |
| 5,173,740 A | * | 12/1992 | Fukuela et al. | 336/246 |
| 5,286,452 A | * | 2/1994 | Hasen | 422/73 |
| 5,412,466 A | * | 5/1995 | Ogino | 356/246 |
| 5,690,895 A | * | 11/1997 | Matsumoto et al. | 422/73 |
| 5,888,823 A | * | 3/1999 | Matsumoto et al. | 436/10 |

FOREIGN PATENT DOCUMENTS

| | | | |
|---|---|---|---|
| JP | 63-94156 | * | 4/1988 |
| JP | 2-32235 | * | 2/1990 |
| JP | A-2176562 | | 7/1990 |
| WO | WO96 04542 | | 2/1996 |

* cited by examiner

Primary Examiner—Maureen M. Wallenhorst

(57) ABSTRACT

A sheath flow cell includes a cell having a guide hole with an inlet and an outlet for guiding a sheath liquid. The cell has a rectifying section, an accelerating section and an orifice section having a cylindrical through-hole, a cone-shaped through-hole tapered toward the outlet and a prism-shaped through-hole with a square shaped section, respectively. The cylindrical, cone-shaped and square prism-shaped through-holes serially and smoothly communicating to each other so as to define the guide hole. There is a sample liquid supply nozzle having a cylindrical shape and extending from the inlet toward the accelerating section co-axially with the through-hole of the rectifying section. The through-hole of the orifice section has a cross section having a side length along its length square of 0.1 mm to 0.4 mm and the through-hole of the rectifying section has an axial length four or more times greater than its inner diameter.

20 Claims, 9 Drawing Sheets

SHEATH FLOW CELL AND BLOOD ANALYZER USING THE SAME

CROSS-REFERENCE TO RELATED APPLICATION

This application is related to Japanese Patent Application No. Hei11(1999)-13293 filed on Jan. 21, 1999, whose priority is claimed under 35 USC §119, the disclosure of which is incorporated by reference in its entirety.

BACKGROUND OF THE INVENTION

1. Field of the Invention

The present invention relates to a sheath flow cell and a blood analyzer using the same, more particularly to a sheath flow cell applicable to a sheath flow system and a multi-parameter blood analyzer using the same.

2. Description of Related Art

Flow cytometers utilizing a so-called sheath flow system are well known as apparatus for analyzing particles such as cells or blood cells in samples. In this system, a sheath liquid envelops and pinches a sample liquid (which contains particles) discharged from a nozzle so that the sample liquid flows thinly in a sheath flow cell, where optical measurement is carried out for counting and analyzing particles in the sample liquid. The term "sheath flow" means a flow in which a flow of a floating particles-containing liquid is narrowed almost to the outer diameter of particles in the center of a sheath liquid which flows in a laminar-flow state within an orifice so that the particles are lined and passed in a row accurately. The sheath flow is utilized for analyzing various kinds of cells in a sample liquid of blood or the like prepared using a dye, a hemolytic agent, a reaction reagent and the like.

Such flow cytometers are desired to provide enhanced operating capability as well as more functions, but they have the disadvantage that measurement using the sheath flow cell and washing thereof take a lot of time. In order to improve the operating capability of flow cytometers, Japanese Unexamined Patent Publication No. Hei 2(1990)-176562 and PCT International Publication No. WO96/04542 disclose analyzers which have a multi-structure nozzle provided with a plurality of inlets for supplying sample liquids so that the sample liquids are introduced into a sheath flow cell via separate passages. The remaining sample liquids in a passage need not be washed away when switched from the one to another for measurement.

However, such a multi-structure nozzle is difficult to be manufactured and assembled and is expensive because of its complicated structure. Furthermore, the operating capability is not expected to improve so much because all the passages of the multiple nozzle must be washed finally after used.

SUMMARY OF THE INVENTION

In view of these circumstances, by studying the fluid characteristics of a flow cell having a simple structure, especially the relationship between flow velocity of a sheath liquid and flow rate of a sample liquid with respect to the configuration of a sheath flow cell, it has been found that the flow rate of the sample liquid can be at least doubled.

Accordingly, the present invention provides a sheath flow cell capable of providing an increased flow rate for sample liquids and a blood analyzer using the same to improve its operating capability.

The present invention provides a sheath flow cell comprising: a cell having a guide hole with an inlet thereto and an outlet therefrom for guiding a sheath liquid, the cell including a rectifying section, an accelerating section and an orifice section having a cylindrical through-hole, a cone-shaped through-hole tapered toward the outlet and a square prism-shaped through-hole, respectively, the cylindrical, cone-shaped and square prism-shaped through-holes serially and smoothly communicating to each other so as to define the guide hole; and a sample liquid supply nozzle having a cylindrical shape and extending from the inlet toward the accelerating section co-axially with the through-hole of the rectifying section, wherein the through-hole of the orifice section has a cross section having a side length of 0.1 mm to 0.4 mm and the through-hole of the rectifying section has an axial length four or more times greater than the inner diameter thereof.

The present invention further provides a blood analyzer comprising: a sheath flow cell as described above; a first supply section and a second supply section for supplying a sheath liquid to the inlet of the sheath flow cell and for supplying a blood-containing sample liquid to the sample liquid supply nozzle, respectively; a light source for irradiating the orifice section with light; a light-receiving section for receiving light emitted from the orifice section; and an analyzing section for analyzing a blood component in the sample liquid on the basis of optical information obtained from the light-receiving section.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
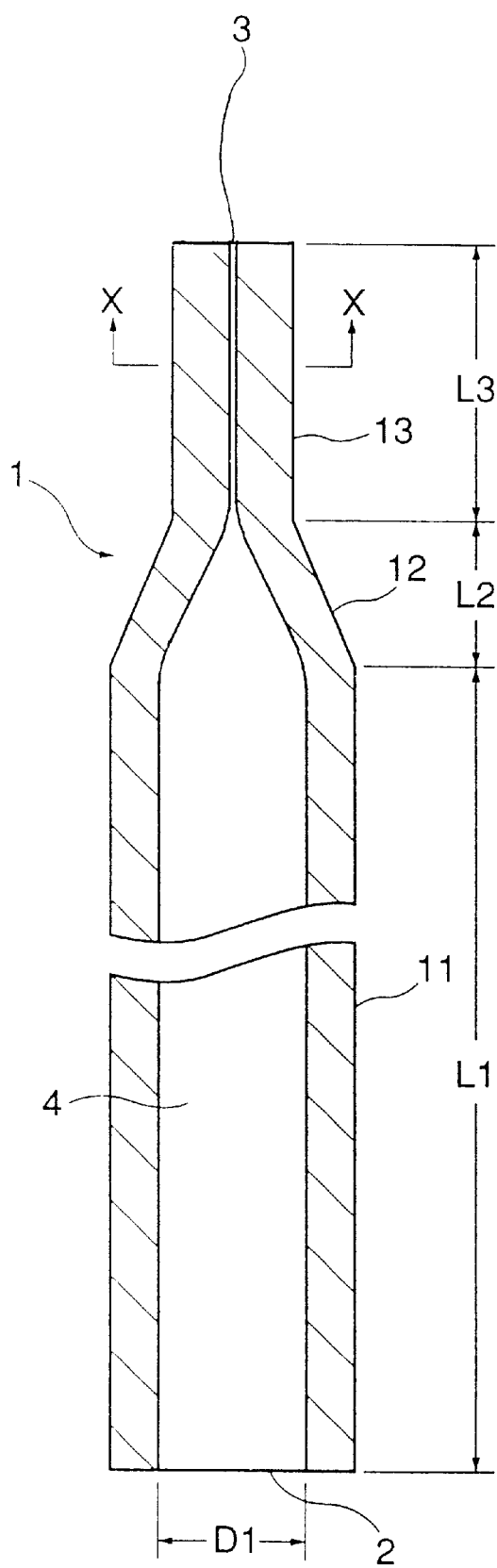
FIG. 1 is a longitudinal sectional view of an example of a cell in accordance with the present invention.

The cell of the present invention has an inlet and an outlet at both ends thereof between which a rectifying section, an accelerating section and an orifice section are serially connected to each other. A guide hole is defined from the inlet to the outlet, by integrally connecting through-holes formed in the sections.

Since the orifice section is irradiated with light for obtaining forward scattered light and side scattered light from particles to be analyzed, the orifice section is preferably constructed of a prism-shaped transparent tube having a square or rectangular cross section. This is for minimizing loss in energy due to refraction or scatter by sidewalls of the orifice section when the orifice section is irradiated with light. In addition to that, if the sidewalls have curved or uneven faces, light is diffused or scattered owing to a lens effect thereof and thus correct information cannot be obtained from light passing through (scattered by particles in) the orifice section.

A material for the orifice section of the cell is not particularly limited and may be any one that can transmit light and has physical and chemical resistance to a liquid passing through the through-hole of the orifice section. For example, the orifice section may be formed of an inorganic glass, a vinyl chloride resin, an acrylic resin and the like. However, the inorganic glass is preferred for the orifice section since resins may sometimes generate air bubbles in the liquid flowing therein. The rectifying section and the accelerating section may be formed of a similar material.

Interior walls of the guide hole must be as smooth as possible in order to let the sheath liquid flow in laminar flow. Conventional cells are produced by cutting operations. However, if the orifice section and the acceleration section are made through cutting operations, the boundary interior wall between the orifice section and the acceleration section may be stepped to provide a shoulder. This is also true of the case where the acceleration section and the rectifying section are made through cutting operations. Further, in the case where the rectifying section is bonded to a member composed of the accelerating section and the orifice section or in the case where a member composed of the rectifying section and the acceleration section to the orifice section, a shoulder having a height of about several hundred micron is always formed on the interior wall at the boundary. Accordingly, as the flow velocity of the sheath liquid is increased, the flow of the sample is disturbed and the measurement of particles cannot be performed. This disturbance is caused by the shoulder on the interior wall of the cell. The shoulder can be avoided by forming the rectifying, accelerating and orifice sections of the cell from the same material and joining them to each other thermally or chemically, for example by welding or fusion-bonding, so that the flow of the sample is not disturbed even if the flow velocity is raised. Particularly, it is preferable that the interior wall of the cell has a smoothly curved surface so that its longitudinal curvature radius is larger than or equal to a side length of the through-hole of the orifice section.

The sample liquid is supplied from the tip of the nozzle into the accelerating section of the cell, thinly pinched by the sheath liquid in the orifice section, and discharged from the outlet. Accordingly, it should be understood that, in order to increase the flow rate of the sample liquid per unit time period into the orifice section, it may be good to increase the flow velocity of the sheath liquid with maintaining it in the laminar-flow state because the flow velocity of the sample liquid at the orifice section almost equals to a central flow velocity of the sheath liquid. For the sheath liquid guided from the inlet to the outlet in the cell, water, a salt solution or the like may be used.

According to the present invention, in the cell whose rectifying section, accelerating section and orifice section are integrally formed and whose guide hole is so formed as to have a smooth interior wall without shoulders, (1) preferably the length of the through-hole in the rectifying section is four or more times greater than its inner diameter; thereby the flow velocity of the sheath liquid can be increased with maintaining its laminar-flow state and consequently the flow rate of the sample liquid per unit time period can be increased to 3 to 10 $\mu$L/sec;

(2) in this case, the through-hole in the orifice section preferably has a square cross section having a side length of 0.1 to 0.4 mm; and (3) also the sheath liquid flowing in the orifice section preferably has an average flow velocity of 6 to 12 m/sec.

The reasons for the above-mentioned (1) to (3) are now explained with reference to the following performance tests.

Figure 2:
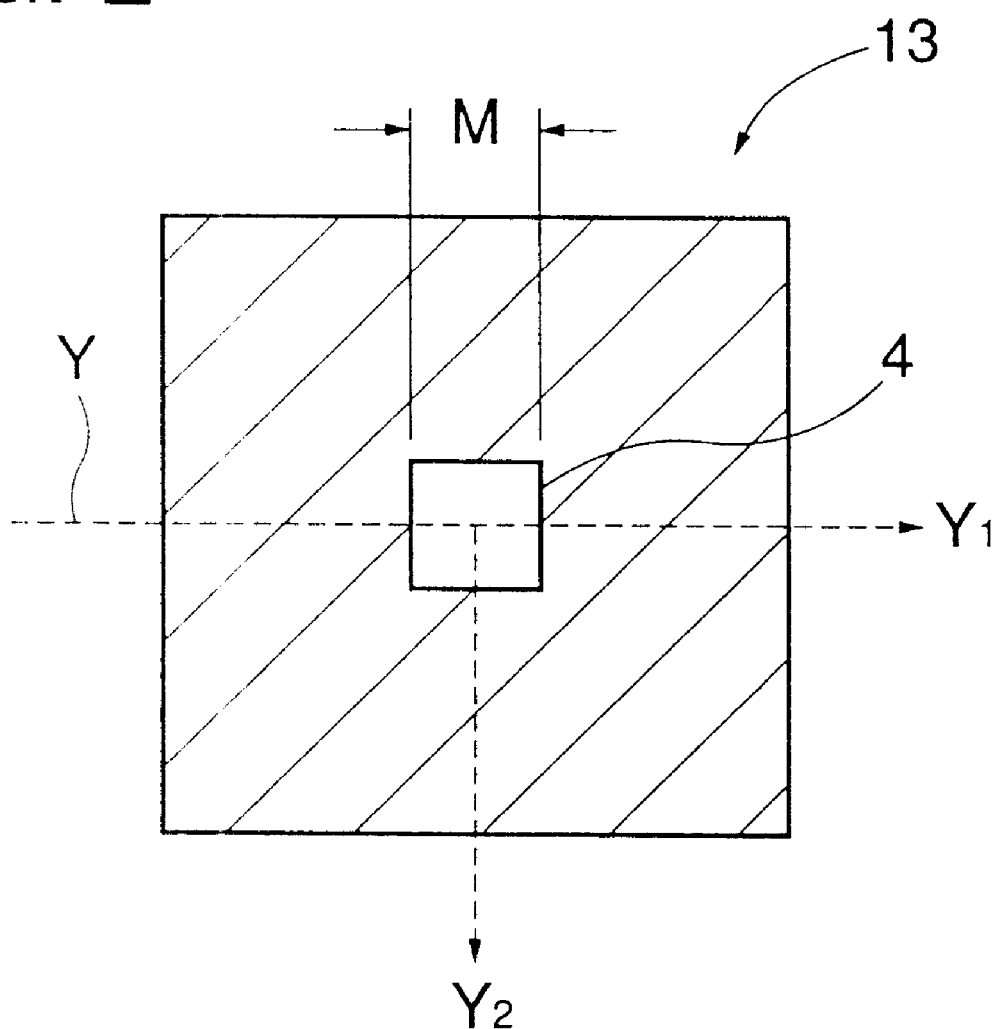
FIG. 2 is an enlarged sectional view as seen in a direction of arrows X, X.

FIG. 1 is a sectional view of an example cell of the sheath flow cell of the present invention, and FIG. 2 is an enlarged sectional view as seen in the direction of arrows X, X of FIG. 1. A cell 1 according to the present invention is provided with a guide hole 4 for guiding a sheath liquid from an inlet 2 to an outlet 3 and includes a rectifying section 11 (of length L1), an accelerating section 12 (of length of L2) and an orifice section 13 (of length of L3) which are continuous from the inlet 2 to the outlet 3.

The rectifying section 11 has a cylindrical through-hole of inner diameter D1 over its length L1, the accelerating section 12 has a cone-shaped through-hole whose diameter gradually decreases toward the outlet 3, and the orifice section 13 has a through-hole whose cross section is shown in FIG. 2 over its length L3. The through-holes are serially connected to form the guide hole 4.

The orifice section 13 of the cell 1 is made up of a prism-shaped transparent tube having a square cross section to obtain good accuracy forward scattered light $Y_1$ and side scattered light $Y_2$ from particles passing through the orifice section 13 which is irradiated with light Y for measuring particles, as shown in FIG. 2.

Figure 3:
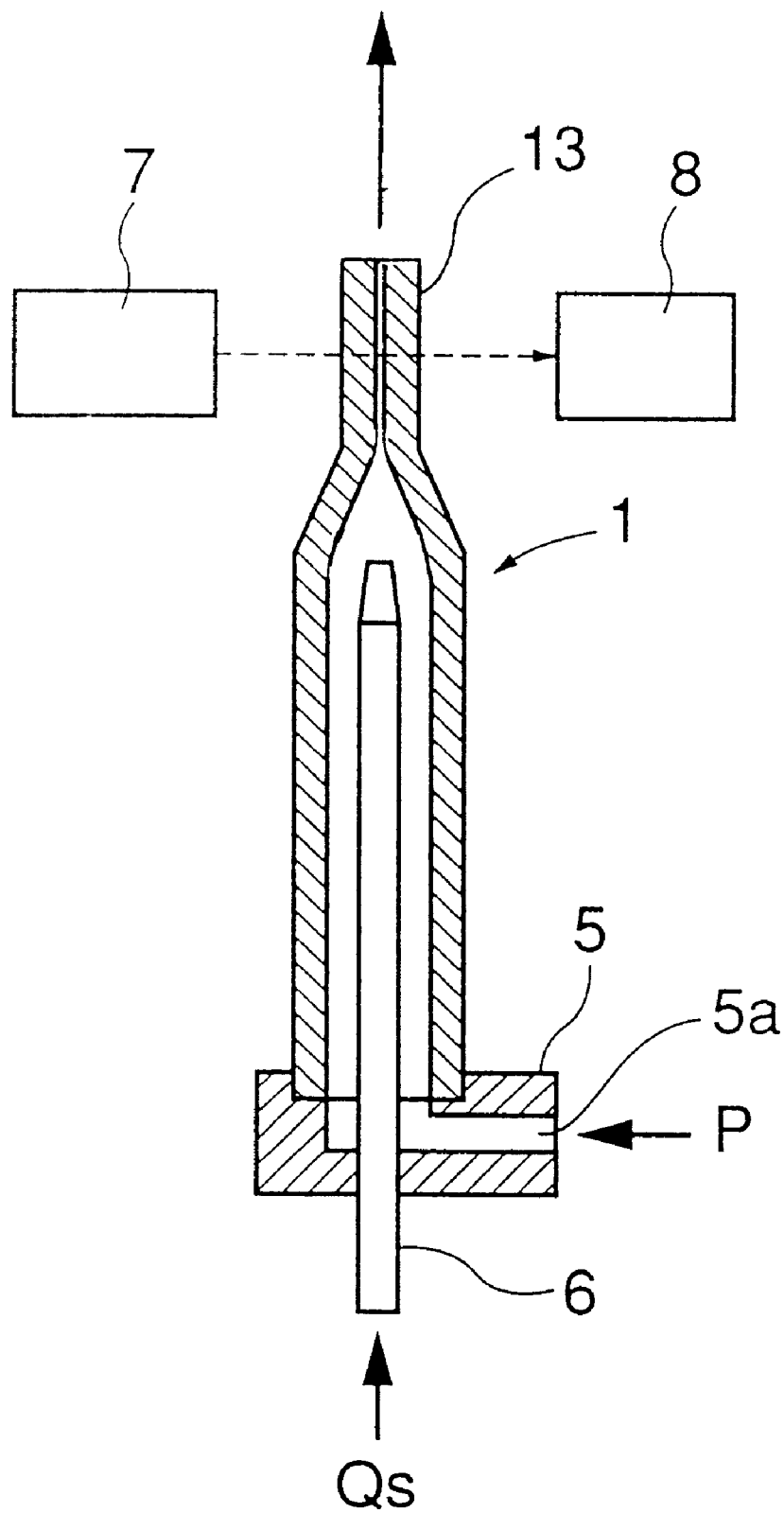
FIG. 3 illustrates how the characteristics of a sheath flow cell in accordance with the present invention are tested.

As shown in FIG. 3, the cell 1 is fixed to a fixing element 5. A nozzle 6 having an outer diameter of 1 mm and an inner diameter of 0.2 mm is inserted into the cell 1 from the inlet 2 so that the tip of the nozzle 6 reached the boundary between the rectifying section 11 and the accelerating section 12 and is fixed to the fixing element 5 co-axially with the rectifying section 11. The sheath liquid is supplied into the cell 1 from an opening 5a of the fixing element 5. At the same time, a diluted ink is supplied as a sample liquid into the nozzle 6. The state of the sheath flow (in laminar flow or in turbulence) is quantitatively observed with varying the length L1 of the rectifying section 11 and the average flow velocity Va of the sheath liquid in the orifice section 13. Here, the supply amount Qs of the sample liquid is set to 4 $\mu$L/sec, which is about two times larger than the conventional supply amount.

For the purpose of observing the state of the flow of the sheath liquid, provided as shown in FIG. 3 are a light source 7 for irradiating the orifice section 13 with light and a video camera 8 for capturing images of the flow of the illuminated sample (ink). Thus measured is the amplitude of the flow of the sample (the amplitude here is a change in width of the flow of the sample in the direction perpendicular to the flow).

Used as the cell 1 are ones which have a constant inner diameter D1 of 5 mm at the rectifying section 11 and have an inner cross section of a square having a side length M of either 0.2 mm or 0.3 mm at the orifice section 13.

Figure 4:
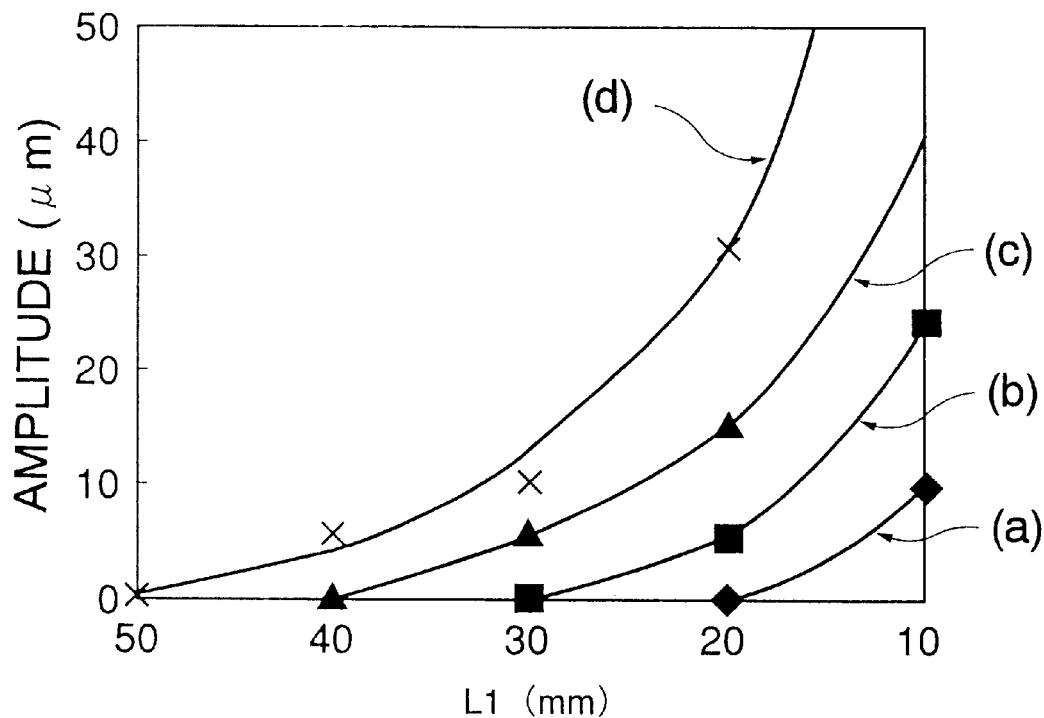
FIG. 4 is a graphical representation showing a relationship between the length of a rectifying section of a sheath flow cell in accordance with the present invention and the amplitude of a flow of a sample liquid.
Figure 5:
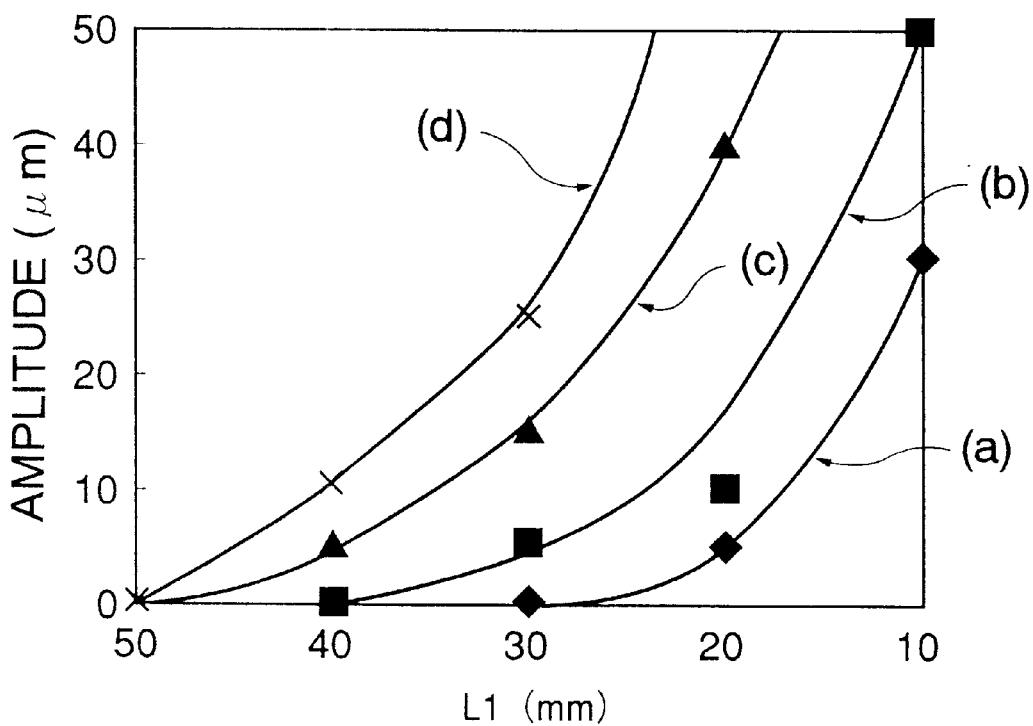
FIG. 5 is a graphical representation showing a relationship between the length of a rectifying section of a sheath flow cell in accordance with the present invention and the amplitude of a flow of a sample liquid.

The results of measurement of the amplitude in the cases of M=0.2 mm and 0.3 mm are shown in FIG. 4 and 5, respectively.

In FIGS. 4 and 5, curves (a), (b), (c) and (d) represents the cases where the average flow velocity Va of the sheath liquid at the orifice section 13 is 6 m/sec 8 m/sec, 10 m/sec and 12 m/sec, respectively.

Table 1 shows conditions found from the results which allow the flow of the sheath liquid at the orifice section 13 to be laminar (the amplitude of the flow of the sample id zero).

TABLE 1

| M (mm) | Va (m/sec) | L1 (mm) | Ds (μm) | P (kg/cm²) |
|---|---|---|---|---|
| 0.2 | 6 | Not less than 20 | 23 | 0.8 |
|  | 8 | Not less than 30 | 20 | 1.3 |
|  | 10 | Not less than 40 | 17 | 1.8 |
|  | 12 | Not less than 50 | 15 | — |
| 0.3 | 9 | Not less than 30 | 22 | 0.5 |
|  | 8 | Not less than 40 | 19 | 0.8 |
|  | 10 | Not less than 50 | 18 | 1.1 |
|  | 12 | Not less than 50 | 15 | 1.5 |

In Table 1, Ds (μm) represents the diameter of the flow of the sample passing through the center of the orifice section 13 and P (kg/cm²) represents the pressure applied for supplying the sheath liquid.

From the results shown in Table 1, conditions for permitting the flow of the sheath liquid to be a laminar flow are as follows:

If Va=6 m/sec, L1≧20 mm, i.e., L1≧4×D1, when M=0.2 mm L1≧30 mm, i.e., L1≧6×D1, when M=0.3 mm;

If Va=10 m/sec, L1≧40 mm, i.e., L1≧8×D1, when M=0.2 mm L1≧50 mm, i.e., L1≧10×D1, when M=0.3 mm.

If Va is increased for further decreasing Ds in correspondence with the diameter of floating particles in the flow of the sample, L1 may be lengthened accordingly.

When components of blood cells in a blood-containing sample liquid are analyzed, the diameter Ds of the flow of the sample is required to be close to the average diameter of blood cells. For example, if Ds is set to be 15 μm as shown in Table 1, it is good that L1≧50 mm (10×D1) when M=0.2 mm and that L1 ≧50 mm (10×D1) when M=0.3 mm.

Further, the characteristics shown in FIGS. 4 and 5 indicate that the laminar flow of the sheath liquid can also be obtained even if L1<20 mm in the case of M=0.1 mm and can be obtained if L1 is about 60 mm to 70 mm even in the case of M=0.4 mm. However, the pressure P for supplying the sheath liquid should be raised as M is decreased.

In the above-described tests, the flow rate Qs of the sample liquid is set for a constant rate of 4 μL/sec. However, it is found out that, even if QS is further varied and set for 10 L/sec or 3 L/sec, for example, the state of the flow of the sheath liquid (conditions for laminar flow) is not affected and only Ds is increased or decreased.

Therefore, it is understood from the above-mentioned results that, according to the present invention, the length of the through-hole of the rectifying section which is four or more times larger than the inner diameter thereof allows the sheath liquid flowing in the orifice section to be laminar even if the sheath liquid is speeded up to 6 m/sec to 12 m/sec in average flow velocity and allows the flow rate of the sample liquid per unit time period to be raised to 3 to 10 μL/sec, which is about 1.5 to 5 times higher than provided by the conventional flow cells. Thus, the operational efficiency of the flow cytometer can be improved. It is also understood that, in this case, the through-hole of the orifice section may have a square cross section having a side length of 0.1 mm to 0.4 mm.

Next, the blood analyzer of the present invention includes the above-described sheath flow cell provided with a combination of the above-described flow cell and the nozzle, a first supply section and a second supply section for supplying a sheath liquid to the inlet and for supplying a blood-containing sample liquid to the sample liquid supply nozzle respectively; a light source for irradiating the orifice section with light; a light-receiving section for receiving light emitted from the orifice section; and an analyzing section for analyzing a blood component in the sample liquid on the basis of optical information obtained from the light-receiving section. The first supply section includes, for example, a sheath liquid chamber for accommodating the sheath liquid, a pressure device, e.g., a compressor and a pressure controller, for applying a constant pressure to the sheath liquid chamber and a supply passage connecting the sheath flow chamber to the inlet of the flow cell via a valve.

The pressure applied to the sheath flow chamber can determine the flow velocity of the sheath liquid in the orifice section.

The second supply section includes, for example, a sampling valve for taking and diluting a certain quantity of collected blood sample, a reaction chamber for treating (diluting, staining, hemolyzing and/or the like) the blood sample and a dispensing syringe for determining a certain quantity of the sample liquid treated in the reaction chamber and supplying the determined sample liquid to the nozzle. In this case, the above-mentioned supply rate Qs (μL/sec) of the sample liquid can be selected as appropriate by selecting a driving speed for the dispensing syringe.

As the light source for irradiating the orifice section of the sheath flow cell with light, usable are a laser diode, an Ar laser, a He-Ne laser and the like. AS shown in FIG. 2, the optical axis of a laser light source is preferably perpendicular to a flat sidewall of the orifice section, which has a square cross section.

Where a lens system is interposed between the light source and the sheath flow cell for adjusting the diameter of a light beam, the adjusted diameter of the light beam is preferably almost equal to the diameter of the flow of the sample in the orifice section. Thereby the flow of the sample is efficiently illuminated.

When the light source illuminates the orifice section with light, the light hits particles in the flow of the sample passing through the orifice to generate forward and side scattered light and side fluorescence.

Accordingly, it is preferable that the light-receiving section includes a photodiode for receiving forward scattered light which has a higher light intensity and a photomultiplier tube for receiving side scattered light and side fluorescence which have a lower light intensity.

In the present invention, the analyzing section extracts and counts blood components contained in the sample liquid on the basis of the optical information obtained by the light-receiving section. The extracted blood components are leukocytes; nucleated erythrocytes; basophils, lymphocytes, monocytes, neutrophils and acidophils which belong to leukocytes; matured erythrocytes; reticulocytes; and blood platelets, for example.

Since the analyzing section is required to have functions for storing the optical information from the light-receiving section, performing classification and computation with reference to the optical information in accordance with a predetermined program, outputting obtained results, etc., the analyzing section is preferably composed of a microcomputer or a personal computer, for example.

EXAMPLE

Now the present invention is described in detail with reference to an example as shown in the accompanying figures. Elements common to the figures are denoted by the same reference numerals and marks.

This example uses a flow cell 1 whose configuration is shown in FIGS. 1 and 2 and which has dimensions of D1=5 mm, L1=50 mm and M=0.2 mm. The cell 1 is integrally formed by fusion-bonding a rectifying section 11, an acceleration section 12 and an orifice section 13 which are each formed of quartz glass.

As shown in FIG. 3, the cell 1 is fixed to a fixing element 5 together with a nozzle 6. A sheath flow cell is thus constructed.

Figure 6:
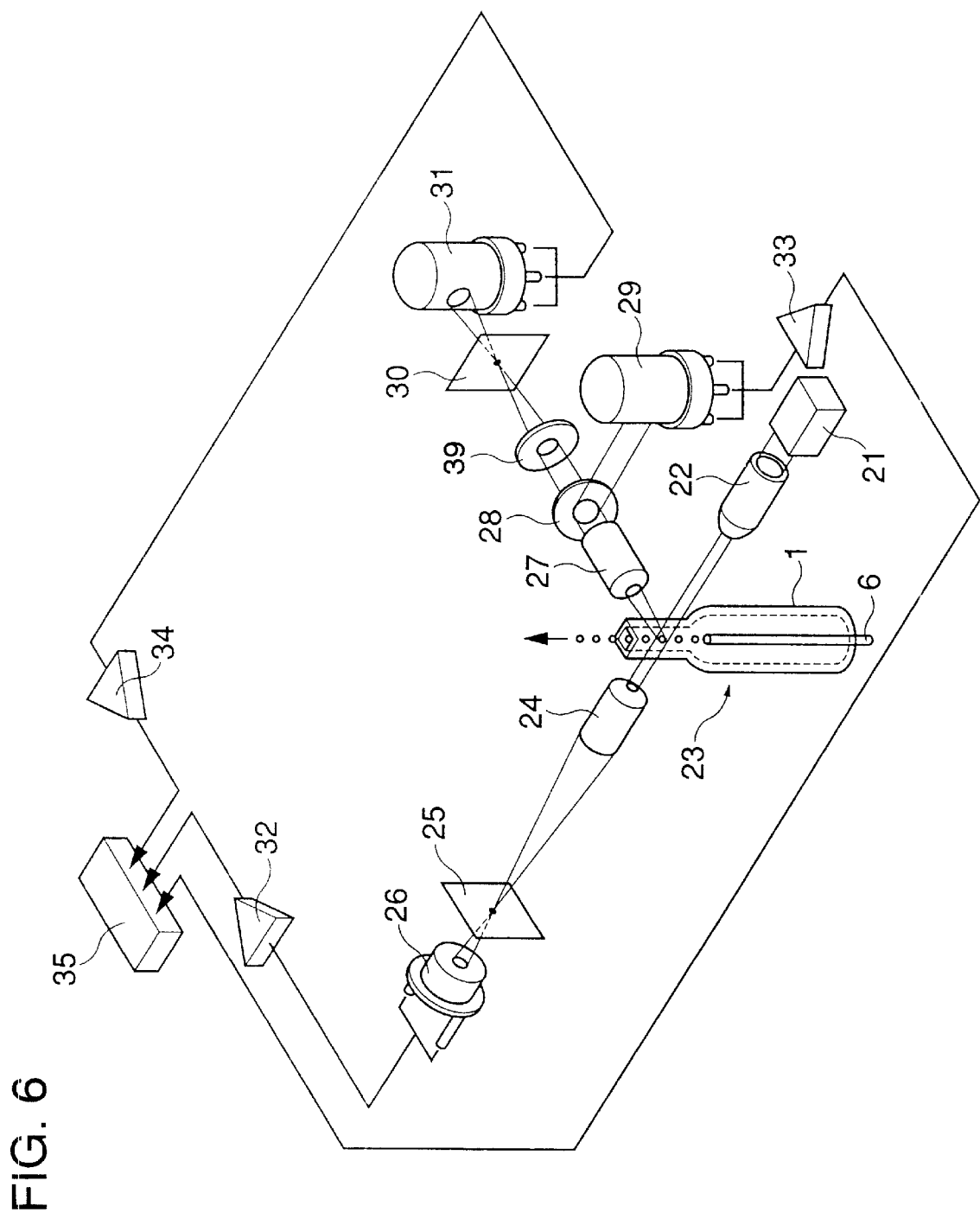
FIG. 6 is a perspective view illustrating an optical system in accordance with an example of the present invention.

FIG. 6 is a perspective view illustrating an optical system of a blood analyzer of the present invention using the above-described sheath flow cell. In this figure, a beam emitted by a laser diode 21 illuminates the orifice section of the sheath flow cell 23 via a collimating lens 22. Forward scattered light emitted by blood cells passing through the orifice section is incident onto a photodiode 26 via a condenser lens 24 and a pinhole plate 25.

As for side scatter light and side fluorescence produced by the blood cells passing through the orifice section, on the other hand, the side scattered light is incident onto a photo-multiplier tube 29 via a condenser lens 27 and a dichroic mirror 28, and the side fluorescence is incident onto a photo-multiplier tube 31 via the condenser lens 27, the dichroic mirror 28, a filter 39 and a pinhole plate 30.

A signal on the forward scattered light which is output by the photodiode 26, a signal on the side scattered light which is output by the photo-multiplier tube 29 and a signal on the side fluorescence which is output by the photo-multiplier tube 31 are amplified by amplifiers 32, 33 and 34, respectively and input to an analyzing section 35.

Figure 7:
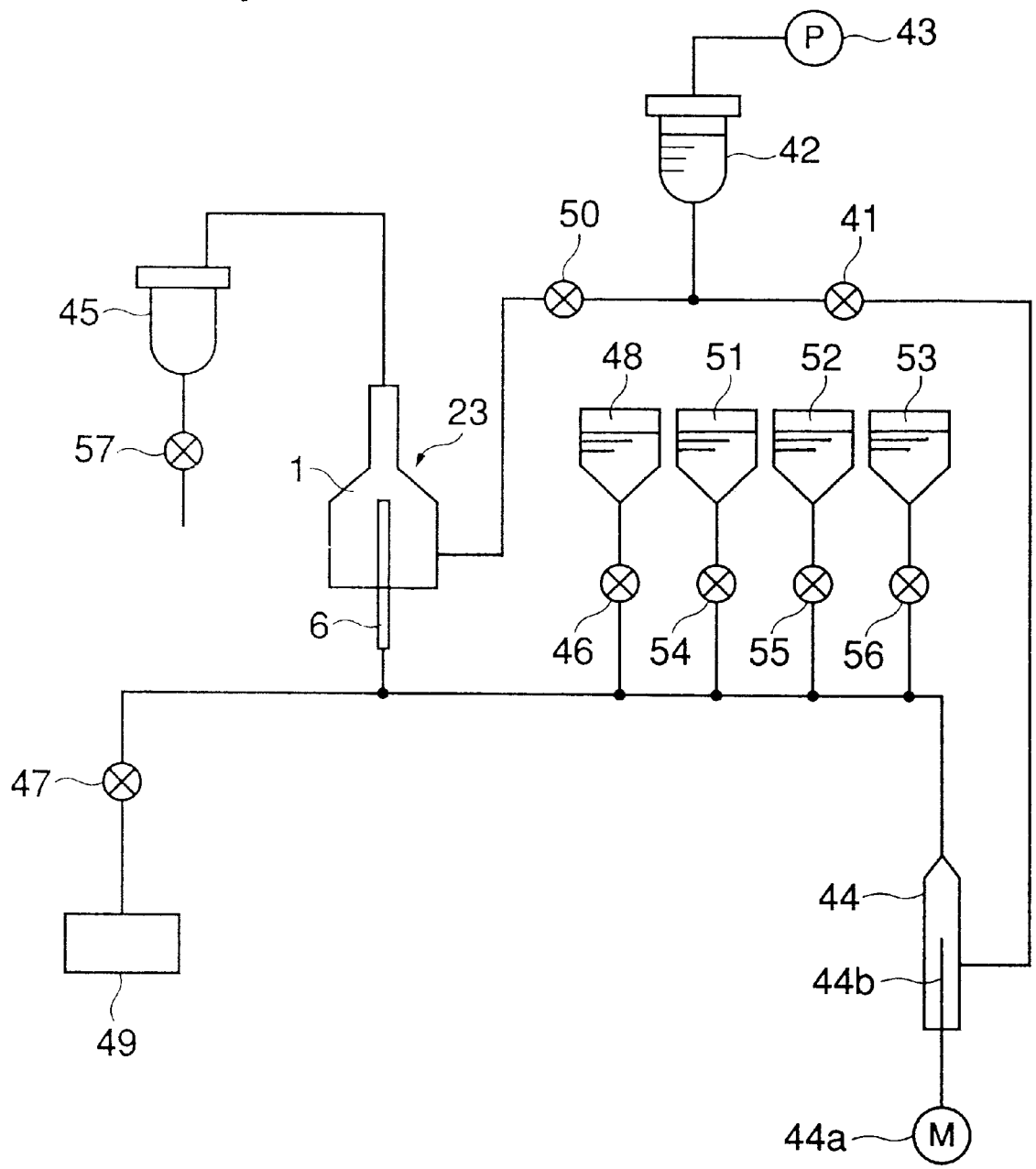
FIG. 7 is a systemic view illustrating a fluid system in accordance with an example of the present invention.

FIG. 7 is a view illustrating a fluid system of the blood analyzer shown in FIG. 6. Referring to this figure, first in a washing process, valves 41 and 50 are opened, the sheath liquid is sent out from a sheath liquid chamber 42 accommodating the sheath liquid by pressure P applied by a pressure device 43. The sheath liquid is discharged into a waste liquid chamber 45 via the valve 41, a dispensing syringe 44 and the nozzle 6 and is simultaneously discharged into the waste liquid chamber 45 via the valve 50 and the cell 1. The valves 41 and 50 are closed after a predetermined time period. Thus the dispensing syringe 44, the nozzle 6, the cell 1 and related passages are washed with the sheath liquid.

Next, in a measurement process, valves 46 and 47 are opened. Then, from a reaction chamber 48 for reacting a blood-containing sample liquid with a reagent and accommodating the resulting sample liquid, the sample liquid is sucked by a negative pressure applied by a suction device 49. When the passage between the valve 46 and the nozzle 6 is filled with the sample liquid, the valves 46 and 47 are closed. Subsequently, the valve 50 is opened, and the sheath liquid is sent out from the sheath liquid chamber 42 to the cell 1 by the pressure from the pressure device 43 and is discharged into the waste liquid chamber 45. At this time, the pressure P applied to the sheath liquid by the pressure device 43 is 1.8 kg/cm$^2$, and the average flow velocity of the sheath liquid is 10 m/sec (see Table 1) at the orifice section 13 (see FIG. 1) of the sheath flow cell 23.

Next, when the valve 41 is opened, the pressure P from the pressure device 43 is also conducted to the tip of the nozzle 6 via the dispensing syringe 44. At the tip of the nozzle 6, the pressure of the sheath liquid outside the nozzle equals the pressure of the sample liquid inside the nozzle. Accordingly, in this state, when a piston 44b of the dispensing syringe 44 is driven by a motor 44a, the sample liquid existing between the valve 46 and the nozzle 6 is easily discharged into the orifice section 13 from the nozzle 6 to be enveloped and pinched by the sheath liquid and passes through the orifice section 13. Then the sample liquid is discharged into the waste liquid chamber 45 together with the sheath liquid.

In this example, the dispensing syringe is driven at such a speed that the flow rate of the sample liquid is 4 μL/sec. The diameter of the flow of the sample liquid pinched in the orifice section 13 is 17 μm (see, Table 1). This value is considered to be proper in view of the average diameter (about 10 μm) of blood cells to be analyzed.

When the driving of the piston 44b of the dispensing syringe 44 is finished, the measurement process is completed.

Next, the motor 44a is reversed to pull the piston 44b back and return the dispensing syringe in its initial state, while at the same time the aforesaid washing process is repeated for preparation for the next measurement process as the vales 41 and 50 remains open.

Accordingly, other sample liquids accommodated in other reaction chambers 51, 52 and 53 can be measured by sequentially opening valves 54, 55 and 56 and repeating the above-described processes.

A valve 57 is a valve for discharging waste liquid from the waste liquid chamber 45 and is opened and closed as required.

Figure 8:
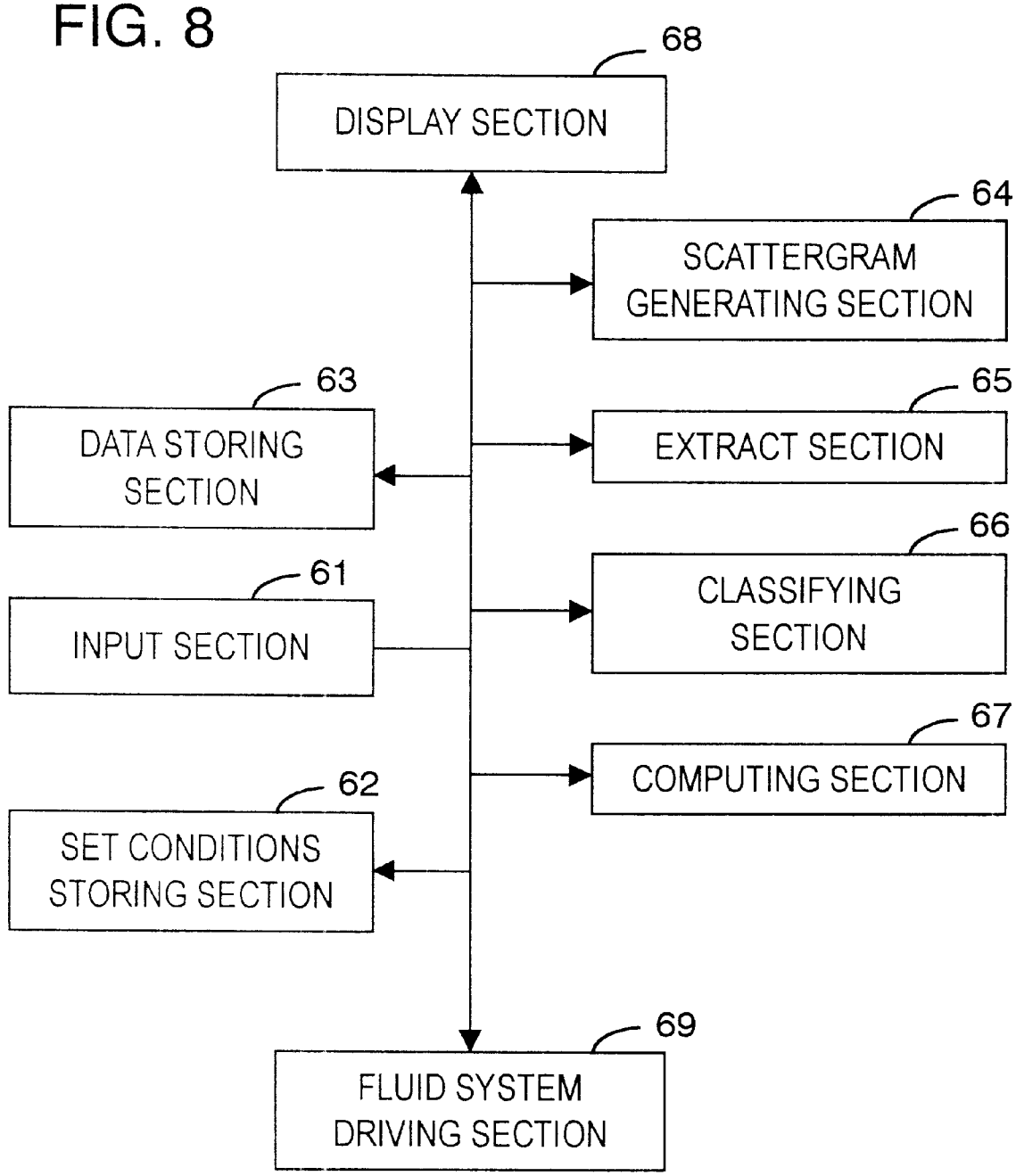
FIG. 8 is a block diagram illustrating the construction of an analyzing unit in accordance with an example of the present invention.

FIG. 8 is a block diagram illustrating the construction of the analyzing section 35 shown in FIG. 6. FIG. 8 shows a data input section 61 for pre-setting conditions such as various numerical values and regions, which is composed, for example, of a keyboard, a mouse or the like.

There are also provided a set conditions storing section 62 for storing the various kinds of settings; a data storing section 63 for storing optical information obtained from output signals from the photodiode 26 and photo-multiplier tubes 29 and 31; a scattergram generating section 64 which generates a two-dimensional scattergram using two parameters out of the optical information, i.e., forward scattered light intensity (Fsc), side scattered light intensity (Ssc) and side fluorescence (Sfl), stored in the data storing section 63; and an extract section 65 which extracts coordinates and regions from the scattergram generated by the scattergram generating section 64.

There are further provided a classifying section 66 for classifying particles and determining areas of the classified particles in the scattergram produced by the scattergram generating section 64 and a computing section 67 for counting the number of particles within the classified area. The results obtained by the computing section 67 are displayed in a display section 68 together with the scattergram produced by the scattergram section 64. A fluid system driving section 69 drives the valves 41, 46, 47, 50, 54, 55, 56 and 57 as well as the motor 44a. The analyzing section 35 is composed of a personal computer.

In the input section 61, with respect to every sample four kinds of modes are selectively input. The four kinds of modes are "nucleated erythrocyte measuring mode," "leukocyte, basophil measuring mode," "leukocyte four-classification mode" and "reticulocyte measuring mode". In correspondence to the input mode, blood quantified by a blood quantifying section not shown and reagents such as a diluent, a dye liquid, a hemolyzing agent and the like are put in the corresponding chamber among the reaction chambers 48, 51, 52 and 53 and are subjected to a necessary treatment. The thus prepared blood sample is sequentially analyzed through the sheath flow cell 1.

In the "nucleated erythrocyte measuring mode," 18 μL of blood and 882 μL of a Stmatlyzer NR hemolyzing agent (produced by Sysmex Corporation) are sent to the reaction chamber 48, to which 18 μL of a Stmatlyzer NR dye are added. The resulting mixture is allowed to react for about seven seconds. Thereby erythrocytes in the blood are hemolyzed, and leukocytes and nucleated erythrocytes are stained.

Figure 9:
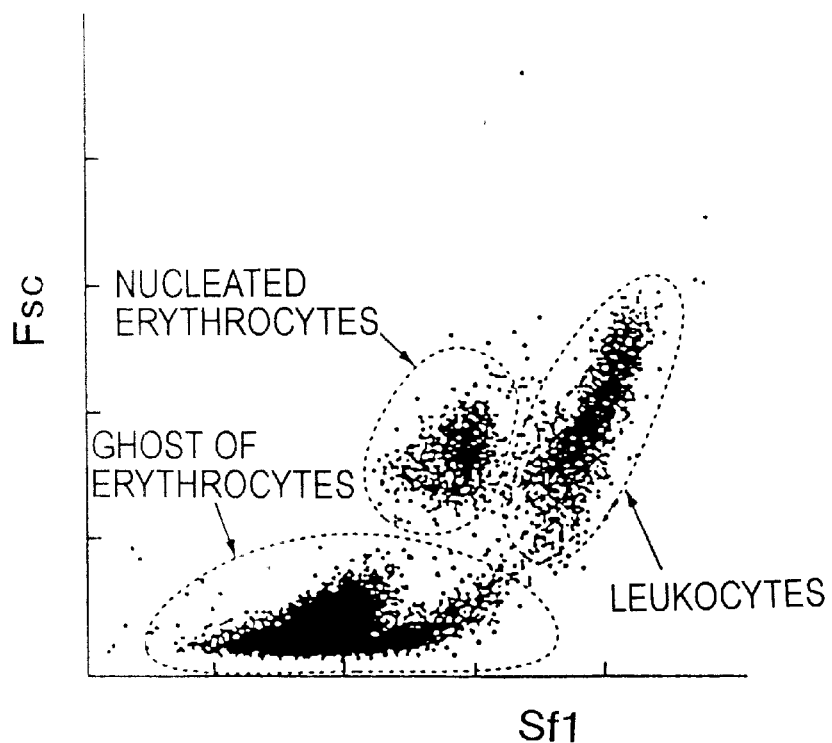
FIG. 9 is an example of display of a scattergram in accordance with an example of the present invention.

The thus treated blood sample is discharge from the nozzle 6 by the dispensing syringe 44 and is optically measured. FIG. 9 is an example of a two dimensional scattergram produced using the side fluorescence intensity (Sfl) and the forward scattered light intensity (Fsc) out of the obtained optical information. Nucleated erythrocytes are demarcated from erythrocytes and leukocytes, and are counted.

In the "leukocyte, basophil measuring mode," 18 μL of blood and 882 μL of a Stmatlyzer FB(II) (produced by Sysmex Corporation) are sent to the reaction chamber 51. The resulting mixture is allowed to react for about 14 seconds. Thereby erythrocytes are hemolyzed, and leukocytes except basophils are contracted and their nuclei are denuded (exposed).

Figure 10:
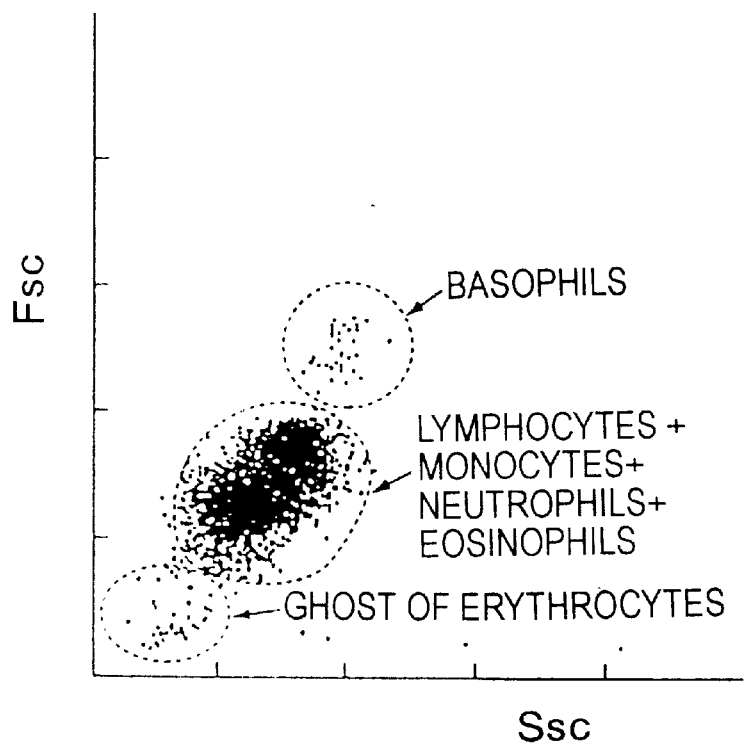
FIG. 10 is an example of display of a scattergram in accordance with an example of the present invention.

The sample thus treated is discharged from the nozzle 6 by the dispensing syringe 44 and is optically measured. FIG. 10 is an example of a two dimensional scattergram produced using the side scattered light intensity (Ssc) and the forward scattered light intensity (Fsc) out of the obtained optical information. Basophils and other leukocytes (including lymphocytes, monocytes, neutrophils and eosinophils) are demarcated and counted.

In the "leukocytes four-classification mode," 18 μL of blood and 882 μL of Stmatlyzer 4DL (produced by Sysmex Corporation) are sent to the reaction chamber 52, to which 18 μL of Stmatlyzer 4DS (produced by Sysmex Corporation) are added. The resulting mixture is allowed to react for about 22 seconds. Thereby erythrocytes are hemolyzed, and leukocytes are stained.

Figure 11:
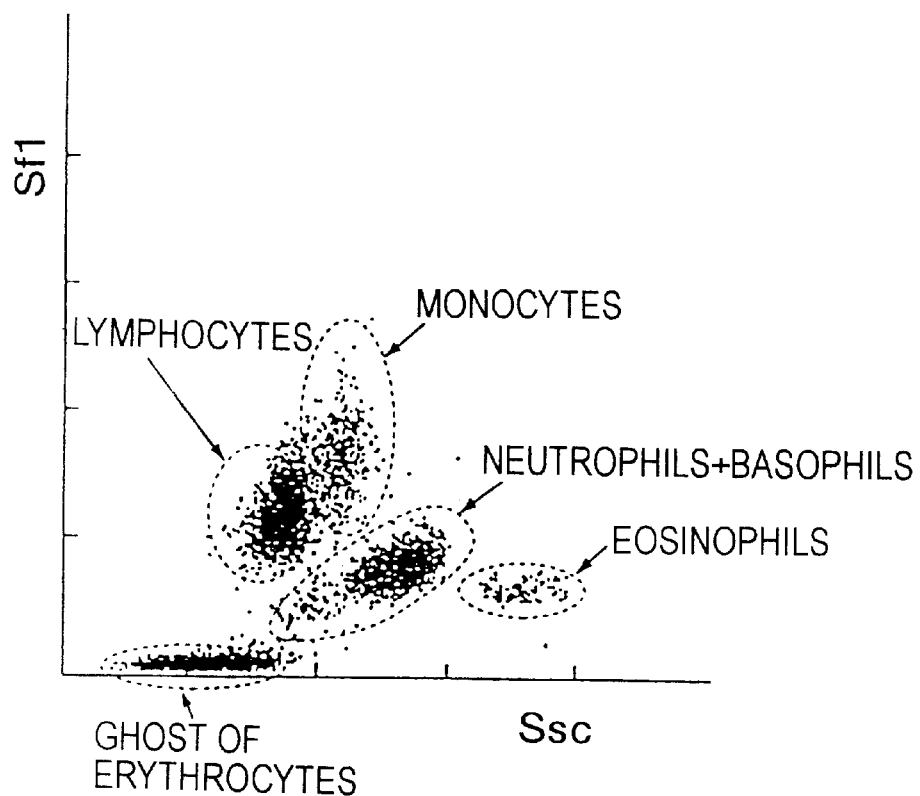
FIG. 11 is an example of display of a scattergram in accordance with an example of the present invention.

The sample thus treated is extruded from the nozzle 6 by the dispensing syringe 44 and is optically measured. FIG. 11 is an example of a two dimensional scattergram produced using the side scattered light intensity (Ssc) and the side fluorescence intensity (Sfl) out of the obtained optical information. Leukocytes are fractioned into lymphocytes, monocytes, neutrophils+basophils, and eosinophils, which are each counted.

In the "reticulocyte measuring mode," 4.5 μL of blood and 895.5 μL of a Retsearch (II) diluent (produced by Sysmex Corporation) are sent to the reaction chamber 53, to which 18 μL of a Retsearch (II) dye (produced by Sysmex Corporation) are added. The resulting mixture is allowed to react for about 31 seconds. Thereby reticulocytes are stained.

Figure 12:
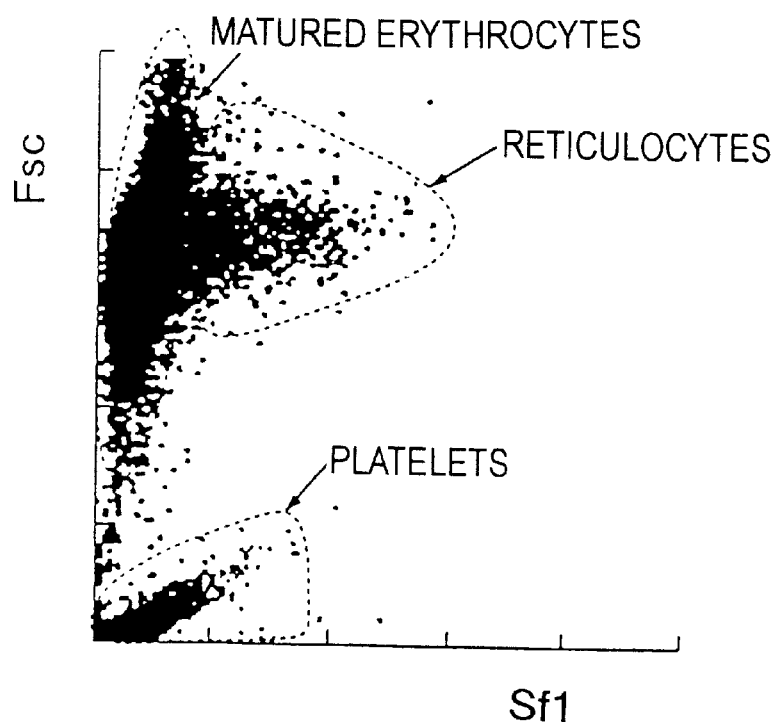
FIG. 12 is an example of display of a scattergram in accordance with an example of the present invention.

The sample thus treated is extruded from the nozzle 6 by the dispensing syringe 44 and is optically measured. FIG. 12 is an example of a two dimensional scattergram produced using the side fluorescence intensity (Sfl) and the forward scattered light intensity (Fsc) out of the obtained optical information. Reticulocytes are distinguished from matured erythrocytes and platelets, and counted In the above-described measurement modes, the sample is measured through the sheath flow cell 1 for about five seconds. Then, for about three seconds, operations including the washing of the nozzle and the sheath flow cell, the switching of passages and the like are conducted, and the analyzer reaches a state of waiting for the next measurement in another next mode. In other words, special analysis such as leukocytes classification and nucleated erythrocytes measurement can be done at a high speed of about eight seconds per measurement mode.

According to the present invention, it is possible to increase the supply amount of a sample liquid per unit time period by constructing a sheath flow cell in such a configuration that allows a high-speed sheath flow to maintain the laminar-flow state. Therefore, the use of this sheath flow cell improves the operating capability of a multi-parameter blood analyzer in terms of time.

What is claimed is:

1. A sheath flow cell comprising:
    a cell having a guide hole with the guide hole having an inlet and an outlet for guiding a sheath liquid, the cell including in sequence from the inlet to the outlet a rectifying section with a cylindrical through-hole, an accelerating section with a cone-shaped through-hole tapered toward the outlet and an orifice section with a prism-shaped through-hole with a square inner cross section, the cylindrical, cone-shaped and prism-shaped through-holes serially and smoothly communicating to each other so as to define the guide hole; and
    a sample liquid supply nozzle having a cylindrical shape and extending from the inlet toward the accelerating section co-axially with the through-hole of the rectifying section,
        wherein the through-hole of the orifice section which has the square-shaped cross section has a side length of 0.1 mm to 0.4 mm extending over the length of the orifice section and the through-hole of the rectifying section has an axial length at least four times greater than the inner diameter thereof.

2. A sheath flow cell according to claim 1, wherein the rectifying section, the accelerating section and the orifice section are integrated by fusion-bonding.

3. A sheath flow cell according to claim 1, wherein the through-holes of the rectifying section, the accelerating section and the orifice section have interior walls which are connected to each other with a longitudinal curvature whose radius is not less than a side length of the through-hole of the orifice section.

4. A blood analyzer comprising:
    a sheath flow cell as set forth in claim 1;
    a first supply section and a second supply section for supplying a sheath liquid to the inlet of the sheath flow cell and for supplying a blood-containing sample liquid to the sample liquid supply nozzle, respectively;

a light source for irradiating the orifice section with light;

a light-receiving section for receiving light emitted from the orifice section; and an analyzing section for analyzing a blood component in the sample liquid on the basis of optical information obtained from the light-receiving section.

5. A blood analyzer according to claim 4, wherein the first supply section supplies the sheath liquid so that the sheath liquid flowing in the orifice section is 6 to 12 m/sec in average flow velocity.

6. A blood analyzer according to claim 4, wherein the second supply section supplies the blood-containing sample liquid to the nozzle at 3 to 10 µL/sec.

7. A blood analyzer according to claim 4, wherein the analyzing section is capable of selectively conducting leukocyte classification measurement, nucleated erythrocyte measurement and reticulocyte measurement on the basis of the optical information.

8. A sheath flow cell comprising:

a cell having a guide hole with the guide hole having an inlet and an outlet for guiding a sheath liquid, the cell including in sequence from the inlet to the outlet a rectifying section with a cylindrical through-hole, an accelerating section with a cone-shaped through-hole tapered toward the outlet and an orifice section with a prism-shaped through-hole with a square inner cross section, the cylindrical, cone-shaped and prism-shaped through-holes serially and smoothly communicating to each other so as to define the guide hole; and a sample liquid supply nozzle having a cylindrical shape and extending from the inlet toward the accelerating section co-axially with the through-hole of the rectifying section, wherein the rectifying section, the accelerating section and the orifice section are integrated by fusion-bonding.

9. A blood analyzer comprising:

a sheath flow cell as set forth in claim 8;

a first supply section and a second supply section for supplying a sheath liquid to the inlet of the sheath flow cell and for supplying a blood-containing sample liquid to the sample liquid supply nozzle, a light source for irradiating the orifice section with light;

a light-receiving section for receiving light emitted from the orifice section; and an analyzing section for analyzing a blood component in the sample liquid on the basis of optical information obtained from the light-receiving section.

10. A blood analyzer according to claim 9, wherein the first supply section supplies the sheath liquid so that the sheath liquid flowing in the orifice section is 6 to 12 m/sec in average flow velocity.

11. A blood analyzer according to claim 9, wherein the second supply section supplies the blood-containing sample liquid to the nozzle at 3 to 10 µL/sec.

12. A blood analyzer according to claim 9, wherein the analyzing section is capable of selectively conducting leukocyte classification measurement, nucleated erythrocyte measurement and reticulocyte measurement on the basis of the optical information.

13. A sheath flow cell comprising:

a cell having a guide hole with the guide hole having an inlet and an outlet for guiding a sheath liquid, the cell including in sequence from the inlet to the outlet a rectifying section with a cylindrical through-hole, an accelerating section with a cone-shaped through-hole tapered toward the outlet and an orifice section with a prism-shaped through-hole with a square inner cross section, the cylindrical, cone-shaped and prism-shaped through-holes serially and smoothly communicating to each other so as to define the guide hole; and a sample liquid supply nozzle having a cylindrical shape and extending from the inlet toward the accelerating section co-axially with the through-hole of the rectifying section, wherein the through-holes of the rectifying section, the accelerating section and the orifice section have interior walls which are connected to each other with a longitudinal curvature whose radius is not less than a side length of the through-hole of the orifice section.

14. A blood analyzer comprising:

a sheath flow cell as set forth in claim 13, a first supply section and a second supply section for supplying a sheath liquid to the inlet of the sheath flow cell and for supplying a blood-containing sample liquid to the sample liquid supply nozzle, a light source for irradiating the orifice section with light;

a light-receiving section for receiving light emitted from the orifice section; and an analyzing section for analyzing a blood component in the sample liquid on the basis of optical information obtained from the light-receiving section.

15. A blood analyzer according to claim 14, wherein the first supply section supplies the sheath liquid so that the sheath liquid flowing in the orifice section is 6 to 12 m/sec in average flow velocity.

16. A blood analyzer according to claim 14, wherein the second supply section supplies the blood-containing sample liquid to the nozzle at 3 to 10 µL/sec.

17. A blood analyzer according to claim 14, wherein the analyzing section is capable of selectively conducting leukocyte classification measurement, nucleated erythrocyte measurement and reticulocyte measurement on the basis of the optical information.

18. A sheath flow cell having a guide hole with an inlet and an outlet, comprising in sequence:

a rectifying section having a cylindrical through-hole;

an accelerating section having a cone-shaped through-hole tapered toward the outlet of the guide hole; and an orifice section having a prism-shaped through-hole with a square inner cross-section, wherein the through-holes of the rectifying section, the accelerating section, and the orifice section serially and smoothly communicate with each other so as to define the guide hole, and wherein the through-hole of the orifice section which has the square-shaped cross section has a side length of 0.1 mm to 0.4 mm extending over the length of the orifice section and the through-hole of the rectifying section has an axial length at least four times greater than the inner diameter thereof.

19. A sheath flow cell having a guide hole with an inlet and an outlet, comprising in sequence:

a rectifying section having a cylindrical through-hole;

an accelerating section having a cone-shaped through-hole tapered toward the outlet of the guide hole; and an orifice section having a prism-shaped through-hole with a square inner cross-section, wherein the through-holes of the rectifying section, the accelerating section, and the orifice section serially and smoothly communicating with each other so as to define the guide hole, and wherein the rectifying section, accelerating section, orifice section are integrated by fusion bounding.

20. A sheath flow cell having a guide hole with an inlet and an outlet, comprising in sequence:

a rectifying section having a cylindrical through-hole;

an accelerating section having a cone-shaped through-hole tapered toward the outlet of the guide hole; and an orifice section having a prism-shaped through-hole with a square inner cross-section, wherein the through-holes of the rectifying section, the accelerating section, and the orifice section serially and smoothly communicate with each other so as to define the guide hole, and wherein the through-holes of the rectifying section, the accelerating section, and the orifice section have interior walls which are connected to each other with a longitudinal curvature whose radius is not less than a side length of the through-hole of the orifice section.

* * * * *